(12) United States Patent
Savage (10) Patent No.: US 10,799,914 B2
(45) Date of Patent: Oct. 13, 2020

(54) METHODS AND SYSTEMS FOR ULTRASONIC LYSIS

(71) Applicant: LUMINEX CORPORATION, Austin, TX (US)

(72) Inventor: Frederick Savage, Austin, TX (US)

(73) Assignee: LUMINEX CORPORATION, Austin, TX (US)

(*) Notice: Subject to any disclaimer, the term of this patent is extended or adjusted under 35 U.S.C. 154(b) by 1759 days.

(21) Appl. No.: 14/293,024

(22) Filed: Jun. 2, 2014

(65) Prior Publication Data

US 2015/0344868 A1 Dec. 3, 2015

(51) Int. Cl.
| | | |
|---|---|---|
| *B06B 1/02* | (2006.01) |
| *C12M 1/00* | (2006.01) |
| *C12N 1/06* | (2006.01) |
| *C12N 13/00* | (2006.01) |

(52) U.S. Cl.
CPC .......... *B06B 1/0246* (2013.01); *C12M 47/06* (2013.01); *C12N 1/06* (2013.01); *C12N 1/066* (2013.01); *C12N 13/00* (2013.01); *B06B 2201/70* (2013.01)

(58) Field of Classification Search
CPC ............ C12N 13/00; B01J 19/10; B06B 3/00
See application file for complete search history.

(56) References Cited

U.S. PATENT DOCUMENTS

| 4,887,299 A * | 12/1989 | Cummins ............ H04R 25/356 |
| | | 381/106 |
| 5,768,939 A | 6/1998 | Quayle et al. |
| 6,397,656 B1 | 6/2002 | Yamaguchi et al. |
| 6,549,860 B1 | 4/2003 | Lillard |
| 6,686,195 B1 | 2/2004 | Colin et al. |
| 6,739,531 B2 * | 5/2004 | Taylor ................... C12N 1/066 |
| | | 241/1 |
| 6,819,027 B2 | 11/2004 | Saraf ........................ 310/316.01 |
| 7,165,451 B1 | 1/2007 | Brooks et al. .................... 73/579 |
| 7,687,039 B2 | 3/2010 | Laugharn, Jr. et al. ...... 422/128 |
| 8,115,366 B2 | 2/2012 | Hoffman et al. ........ 310/316.01 |
| 2008/0129146 A1 | 6/2008 | Puskas |
| 2010/0049098 A1* | 2/2010 | Shalgi ...................... A61N 7/02 |
| | | 601/2 |
| 2012/0295269 A1 | 11/2012 | Pourahmadi et al. |
| 2013/0251222 A1 | 9/2013 | Huang |
| 2013/0302213 A1 | 11/2013 | Lipkens et al. |

FOREIGN PATENT DOCUMENTS

WO  WO 2014/135987  9/2014

OTHER PUBLICATIONS

International Search Report and Written Opinion, issued in PCT/US2015031478, dated Nov. 3, 2015.
Invitation to Pay Additional Fees, issued in PCT/US2015031478, dated Aug. 21, 2015.

* cited by examiner

*Primary Examiner* — Renee Claytor
*Assistant Examiner* — Susan E. Fernandez
(74) *Attorney, Agent, or Firm* — Parker Highlander PLLC

(57) ABSTRACT

Methods and systems for cell lysis are disclosed. Particular embodiments relate to applying acoustic energy to a biological sample located in a sample chamber.

17 Claims, 7 Drawing Sheets

METHODS AND SYSTEMS FOR ULTRASONIC LYSIS

FIELD OF THE INVENTION

Embodiments of the present invention relate to cell lysis. Particular embodiments relate to applying acoustic energy to a biological sample located in a sample chamber.

BACKGROUND

The following descriptions and examples are not admitted to be prior art by virtue of their inclusion within this section.

Various cell disruption techniques can be used to break open cells, including for example, bead milling, freeze fracturing, enzymic digestion, or osmotic lysis. In certain examples, acoustic—and specifically ultrasonic—energy can be applied to cells to achieve lysis. Ultrasonic energy may also be used for improving lysis time performed with other methods, or eliminating altogether the need for other lysis methods. Ultrasonic lysis has been shown to release DNA from difficult to lyse specimens such as *Bacillus Anthracis* spores. Existing acoustic or ultrasonic lysis systems include those disclosed in U.S. Pat. Nos. 6,686,195 and 8,115,366, which are incorporated herein by reference.

SUMMARY OF THE INVENTION

Exemplary embodiments of the present disclosure relate to systems and methods for cell lysis. Particular embodiments relate to systems and methods for applying acoustic energy to a biological sample located in a sample chamber.

Certain existing acoustic cell lysis systems attempt to determine a resonant frequency of the target sample or system by determining the frequency at which the energy reflected from or transmitted through the sample has the highest intensity.

In contrast, exemplary embodiments of the present disclosure determine a frequency in which the energy reflected from or transmitted through the sample has a minimized intensity (e.g. an intensity that is at or near the minimum value of reflected or transmitted intensity within the range of frequencies for the transmitted or reflected energy). By determining a minimized value of the reflected or transmitted intensity, an optimized frequency transmit frequency can be determined (e.g. a frequency at or near the frequency in which a maximum value of energy is lysing cells rather than passing through the chamber.) Certain methods described in this disclosure can also involve an additional transducer that measures the acoustic energy directly. Methods described in this disclosure utilize the actual measurable acoustic energy for determining the optimal transmit frequency for ultrasonic lysis.

Another advantage of locating the frequency for delivering maximum acoustic energy to the sample is the ability to use smaller power amplifier electronics. Typically, ultrasonic transducers are driven from large power sources that require upwards of several hundred watt power amplifier electronics. By locating the maximum acoustic energy delivered to the system, it is possible to reduce the required power rating for the driving circuitry. This can result in a reduction in size and potentially a reduction in radiated electronic emissions, which are issues that typically follow high power amplifier electronics.

Exemplary embodiments are therefore configured to apply maximum acoustic energy to a biological sample located in a sample chamber to achieve cell lysis. Systems and methods using a single ultrasonic transducer, as well as systems and methods using two ultrasonic transducers are disclosed.

In exemplary embodiments, the coupling method for applying an ultrasonic transducer to a sample chamber could be spring based or directly coupled to the cartridge. In certain exemplary embodiments, the range of frequencies can vary from 10 kHz-100 kHz. The frequency of the electrical signal applied to the ultrasonic transducer element can produce an acoustic signal of the same frequency. This adjustable range can allow a user to sweep values until a maximum peak value for energy dissipation is determined.

Certain embodiments include a method that may comprise: (a) operating an ultrasonic transducer to transmit acoustic energy at a series of transmission frequencies into a chamber; (b) receiving, with the ultrasonic transducer, reflected acoustic energy from the chamber; (c) determining an optimized transmit frequency, wherein the optimized transmit frequency is a transmit frequency that produces a minimized value of the reflected acoustic energy from the chamber; and (d) operating the ultrasonic transducer to transmit acoustic energy at the optimized transmit frequency into the chamber.

In particular embodiments, determining the optimized transmit frequency may comprise: measuring a value of the reflected acoustic energy from the chamber at multiple transmit frequencies to obtain a plurality of reflected acoustic energy values; applying a polynomial function to the plurality of reflected acoustic energy values; and determining a transmit frequency that corresponds with a minimum value of the polynomial function, where the transmit frequency that corresponds with the minimum value of the polynomial function is the optimized transmit frequency. In specific embodiments, the ultrasonic transducer may be operated to transmit acoustic energy at the optimized transmit frequency into the chamber for a predetermined period of time. In certain embodiments, the predetermined period of time may be between 5 seconds and 5 minutes, or between 10 seconds and 2 minutes, or between 20 seconds and 1 minute.

In particular embodiments, the series of transmission frequencies may span a range of 10 kHz-100 kHz, or a range of 20 kHz-80 kHz, or a range of 40 kHz-60 kHz. In specific embodiments, the optimized transmit frequency may be between 30 kHz-60 kHz, or between 40 kHz-50 kHz.

In specific embodiments, the series of transmission frequencies may be transmitted at finite frequency stepped responses. In certain embodiments, the series of transmission frequencies may be initially transmitted at 5 kHz intervals. In particular embodiments, the series of transmission frequencies may be subsequently transmitted at 1 kHz intervals between the two transmission frequencies that produced the lowest two values of reflected energy from the chamber.

In specific embodiments, the series of transmission frequencies may be transmitted as a frequency-modulated (FM) sweep. In some embodiments, the operating the ultrasonic transducer to transmit the series of transmission frequencies into the chamber and the receiving with the ultrasonic transducer the series of reflected frequencies from the chamber may be completed in less than 10 seconds. In certain embodiments, the minimized value of the reflected acoustic energy from the chamber may be a minimum value of the reflected acoustic energy from the chamber corresponding to any frequency within the series of transmission frequencies. In particular embodiments, the minimized value of the reflected acoustic energy from the chamber may be within one percent, or five percent, or ten percent, or twenty percent of a minimum value of the reflected acoustic energy from the chamber.

In some embodiments, a wall of the chamber opposite the ultrasonic transducer may comprise a material that reflects ultrasonic energy. In particular embodiments, a wall of the chamber opposite the ultrasonic transducer may be adjacent to a reflecting surface that comprises a material that reflects ultrasonic energy. In certain embodiments, the reflecting surface may have an acoustic impedance that is at least five percent, or ten percent, or twenty percent, or fifty percent different than an acoustic impedance of the wall of the chamber opposite the ultrasonic transducer.

In specific embodiments, the ultrasonic transducer may alternatingly transmit acoustic energy for between 5 to 50 frequency cycles, then may receive reflected acoustic energy for between 1 to 10 frequency cycles. In certain embodiments, the chamber may contain a sample comprising a known cell type and/or virus type, and the method may further comprise storing an identifier of the known cell type and the transmit frequency.

Particular embodiments may include a method comprising: (a) operating an ultrasonic transducer to alternatingly transmit acoustic energy to and receive acoustic energy from a chamber over a series of multiple, different frequencies; (b) determining an optimized transmit frequency that produces a minimized reflected energy from the chamber; and (c) operating the ultrasonic transducer to transmit the optimized transmit frequency into the chamber.

In certain embodiments, the ultrasonic transducer may be operated to transmit acoustic energy at the optimized transmit frequency into the chamber for a predetermined period of time.

Particular embodiments may include a method comprising: (a) operating an ultrasonic transducer to transmit acoustic energy at a series of transmission frequencies into a chamber; (b) receiving, with the ultrasonic transducer, reflected acoustic energy from the chamber; (c) determining a reflection coefficient (R), wherein the reflection coefficient is a ratio of reflected acoustic energy intensity ($I_{reflected}$) and transmitted acoustic energy intensity ($I_{transmitted}$), at a plurality of transmit frequencies; and (d) operating the ultrasonic transducer to transmit acoustic energy into the chamber at a transmit frequency corresponding to: a minimum determined value of R, where $R=I_{reflected}/I_{transmitted}$, or a maximum determined value of R, where $R=I_{transmitted}/I_{reflected}$.

In certain embodiments, the ultrasonic transducer may be operated to transmit acoustic energy into the chamber corresponding to a minimum or maximum value of R for a predetermined amount of time. In some embodiments, the chamber may contain a sample comprising a known cell type and/or virus type, the method further comprising storing an identifier of the known cell type, the transmit frequency, and the minimum or maximum determined value of R in a relational database.

Particular embodiments may include a method comprising: (a) operating a first ultrasonic transducer to transmit acoustic energy at a series of frequencies to a chamber; (b) operating a second ultrasonic transducer to receive acoustic energy from the chamber while the first ultrasonic transducer transmits the acoustic energy to the chamber; (c) determining a reception coefficient (R), wherein the reception coefficient is a ratio of received acoustic energy intensity ($I_{received}$) and transmitted acoustic energy intensity ($I_{transmitted}$), at a plurality of transmit frequencies; and (d) operating the first ultrasonic transducer to transmit acoustic energy into the chamber at a transmit frequency corresponding to: a minimum determined value of R, where $R=I_{received}/I_{transmitted}$, or a maximum determined value of R, where $R=I_{transmitted}/I_{received}$.

In specific embodiments, the chamber may contain a sample comprising a known cell type and/or virus type, the method further comprising storing an identifier of the known cell type, the transmit frequency, and the minimum or maximum determined value of R in a relational database.

Certain embodiments may include a method comprising: (a) operating a first ultrasonic transducer to transmit a first series of frequencies to a chamber; (b) operating a second ultrasonic transducer to receive acoustic energy from the chamber while the first ultrasonic transducer transmits the series of frequencies to the chamber; (c) determining a first reception coefficient (R1), wherein the first reception coefficient is a ratio of acoustic energy intensity received by the second ultrasonic transducer ($I2_{received}$) and acoustic energy intensity transmitted by the first ultrasonic transducer ($I1_{transmitted}$) by, at a plurality of transmit frequencies; (d) operating the second ultrasonic transducer to transmit a second series of frequencies to the chamber; (e) operating the first ultrasonic transducer to receive acoustic energy from the chamber while the second ultrasonic transducer transmits the second series of frequencies to the chamber; (f) determining a second reception coefficient (R2), wherein the second reception coefficient is a ratio of acoustic energy intensity received by the first ultrasonic transducer ($I1_{received}$) and acoustic energy intensity transmitted by the second ultrasonic transducer ($I2_{transmitted}$) by, at a plurality of transmit frequencies; and (g) operating the first and second ultrasonic transducers to transmit acoustic energy into the chamber at a transmit frequency corresponding to: a minimum determined value of R1, where $R1=I2_{received}/I1_{transmitted}$; a maximum determined value of R1, where $R1=I2_{transmitted}/I1_{received}$; a minimum determined value of R2, where $R2=I1_{received}/I2_{transmitted}$; or a maximum determined value of R2, where $R2=I1_{transmitted}/I2_{received}$.

In particular embodiments, the chamber may contain a sample comprising a known cell type and/or virus type, the method further comprising storing an identifier of the known cell type, the transmit frequency, and the minimum or maximum determined value of R1 and R2 in a relational database.

Some embodiments may include a method comprising: (a) operating an ultrasonic transducer to transmit, into a chamber containing a specified cell and/or virus, acoustic energy at a predetermined frequency corresponding to a predetermined reflection coefficient ($R_{predetermined}$) for the specified cell type, wherein the reflection coefficient is a ratio of reflected acoustic energy intensity ($I_{reflected}$) and transmitted acoustic energy intensity ($I_{transmitted}$); (b) intermittently operating the ultrasonic transducer to receive reflected acoustic energy from the chamber; (c) determining a calculated reflection coefficient ($R_{calculated}$); (d) continuing to operate the ultrasonic transducer at the predetermined frequency if the calculated reflection coefficient ($R_{calculated}$) is within a predefined range of the predetermined reflection coefficient ($R_{predetermined}$) or, if the calculated reflection coefficient ($R_{calculated}$) is outside the predefined range of the predetermined reflection coefficient ($R_{predetermined}$), adjusting the transmit frequency of the ultrasonic transducer until the calculated reflection coefficient ($R_{calculated}$) is within the predefined range of the predetermined reflection coefficient ($R_{predetermined}$); and (e) terminating operation of the ultrasonic transducer after a period of time sufficient to lyse the specified cell and/or virus.

In specific embodiments, adjusting the transmit frequency of the ultrasonic transducer may comprise: (a) operating the ultrasonic transducer to transmit acoustic energy at a series of transmission frequencies into the chamber; (b) receiving, with the ultrasonic transducer, reflected acoustic energy from the chamber. In certain embodiments, the ultrasonic transducer may alternatingly transmit acoustic energy for between 5 to 50 frequency cycles, then receive reflected acoustic energy for between 1 to 10 frequency cycles.

Certain embodiments may include a method comprising: (a) operating a first ultrasonic transducer to transmit, into a chamber containing a specified cell and/or virus, acoustic energy at a predetermined frequency corresponding to a predetermined reflection coefficient ($R_{predetermined}$) for the specified cell type, wherein the reflection coefficient is a ratio of reflected acoustic energy intensity ($I_{reflected}$) and transmitted acoustic energy intensity ($I_{transmitted}$); (b) intermittently operating the ultrasonic transducer to receive reflected acoustic energy from the chamber; (c) determining a calculated reflection coefficient ($R_{calculated}$); (d) continuing to operate the ultrasonic transducer at the predetermined frequency if the calculated reflection coefficient ($R_{calculated}$) is within a predefined range of the predetermined reflection coefficient ($R_{predetermined}$) or, if the calculated reflection coefficient ($R_{calculated}$) is outside the predefined range of the predetermined reflection coefficient ($R_{predetermined}$), adjusting the transmit frequency of the ultrasonic transducer until the calculated reflection coefficient ($R_{calculated}$) is within the predefined range of the predetermined reflection coefficient ($R_{predetermined}$); and (e) terminating operation of the ultrasonic transducer after a period of time sufficient to lyse the specified cell and/or virus.

Certain embodiments may include a method comprising: (a) operating a first ultrasonic transducer to transmit acoustic energy at a series of frequencies to a chamber; (b) operating a second ultrasonic transducer to receive acoustic energy from the chamber while the first ultrasonic transducer transmits the acoustic energy to the chamber; (c) determining an optimized transmit frequency, wherein the optimized transmit frequency is a transmit frequency at which the second ultrasonic transducer receives a minimized value of acoustic energy from the chamber; and (d) operating the first ultrasonic transducer to transmit acoustic energy at the optimized transmit frequency into the chamber.

In particular embodiments, the first ultrasonic transducer may be operated to transmit acoustic energy at the optimized transmit frequency into the chamber for a predetermined period of time. In some embodiments, the predetermined period of time may be between 5 seconds and 5 minutes, or between 10 seconds and 2 minutes, or between 30 seconds and 1 minute.

In some embodiments, the minimized value of the reflected acoustic energy from the chamber may be a minimum value of the reflected acoustic energy from the chamber corresponding to any frequency within the series of transmission frequencies. In particular embodiments, the minimized value of the reflected acoustic energy from the chamber may be within one percent, or five percent, or ten percent, or twenty percent of a minimum value of the reflected acoustic energy from the chamber.

In certain embodiments, the chamber may contain a sample comprising a known cell type and/or virus type, the method further comprising storing an identifier of the known cell type, the transmit frequency, and the minimum or maximum determined value of R in a relational database.

Particular embodiments may include a method comprising: (a) operating a first ultrasonic transducer to transmit a first series of frequencies to a chamber; (b) operating a second ultrasonic transducer to receive acoustic energy from the chamber while the first ultrasonic transducer transmits the series of frequencies to the chamber; (c) determining a first optimized transmit frequency, wherein the first optimized transmit frequency is a transmit frequency at which the second ultrasonic transducer receives minimum acoustic energy from the chamber; (d) operating the second ultrasonic transducer to transmit a second series of frequencies to the chamber; (e) operating the first ultrasonic transducer to receive acoustic energy from the chamber while the second ultrasonic transducer transmits the second series of frequencies to the chamber; (f) determining a second optimized transmit frequency, wherein the second optimized transmit frequency is a transmit frequency at which the first ultrasonic transducer receives minimum acoustic energy from the chamber; (g) operating the first ultrasonic transducer to transmit the first optimized transmit frequency into the chamber and operating the second ultrasonic transducer to transmit the second optimized transmit frequency into the chamber for a predetermined amount of time.

In certain embodiments, the first and second optimized transmit frequencies may be the same, and in some embodiments, the first and second optimized transmit frequencies may be different. In particular embodiments, the first and second optimized transmit frequencies may be transmitted to the chamber simultaneously. In specific embodiments, the first and second optimized transmit frequencies may be transmitted to the chamber in an alternating pattern. In particular embodiments, the chamber may contain a sample comprising a known cell type and/or virus type, the method further comprising storing an identifier of the known cell type and the transmit frequency.

Specific embodiments may include a computer-implemented method comprising: (a) operating an ultrasonic transducer with a computer processor to transmit acoustic energy at a series of transmission frequencies into a chamber; (b) receiving, with the ultrasonic transducer, reflected acoustic energy from the chamber; (c) storing values for the reflected acoustic energy in a computer memory; (d) accessing the values for the reflected acoustic energy with the computer processor; (e) determining an optimized transmit frequency with the computer processor, wherein the optimized transmission frequency is a transmit frequency that produces a minimized value of the reflected acoustic energy from the chamber; and (f) operating the ultrasonic transducer with the computer processor to transmit acoustic energy at the optimized transmit frequency into the chamber.

Particular embodiments may include a computer-implemented method comprising: (a) operating a first ultrasonic transducer with a computer processor to transmit a first series of frequencies to a chamber; (b) operating a second ultrasonic transducer with the computer processor to receive acoustic energy from the chamber while the first ultrasonic transducer transmits the series of frequencies to the chamber; (c) storing values for the acoustic energy received by the second ultrasonic transducer in a computer memory; (d) accessing the values for the acoustic energy received by the second ultrasonic transducer with the computer processor; (e) determining with the computer processor a first optimized transmit frequency, wherein the first optimized transmit frequency is a transmit frequency at which the second ultrasonic transducer receives a minimized value of the acoustic energy from the chamber; (f) operating the second ultrasonic transducer with the computer processor to transmit a second series of frequencies to the chamber; (g) operating the first ultrasonic transducer with the computer processor to receive acoustic energy from the chamber while the second ultrasonic transducer transmits the second series of frequencies to the chamber; (h) storing values for the acoustic energy received by the first ultrasonic transducer in the computer memory; (i) accessing the values for the acoustic energy received by the first ultrasonic transducer with the computer processor; (j) determining with the computer processor a second optimized transmit frequency, wherein the second optimized transmit frequency is a transmit frequency at which the first ultrasonic transducer receives a minimized value of the acoustic energy from the chamber; and (k) operating the first ultrasonic transducer with the computer processor to transmit the first optimized transmit frequency into the chamber and operating the second ultrasonic transducer with the computer processor to transmit the second optimized transmit frequency into the chamber for a predetermined amount of time.

Specific embodiments may include an electronic circuit configured to transmit and receive electric signals corresponding to acoustic energy, the electronic circuit comprising: (a) a switch; (b) an amplifier circuit; (c) an analog to digital converter; (d) a power amplifier circuit; and (e) a processor programmed with instructions to control the power amplifier circuit. In particular embodiments, the switch may be a multi-wound transformer, a single-wound transformer, or a solid state switching device. In certain embodiments, the power amplifier circuit may comprise a field-effect transistor. In particular embodiments, the processor may be a microprocessor, microcontroller, field-programmable gate array, or digital signal processor. In certain embodiments, the processor may be configured to transmit electric signals to an ultrasonic transducer and receive electric signals from the ultrasonic transducer. In specific embodiments, the processor may be configured to transmit electric signals to the ultrasonic transducer and receive electric signals from the ultrasonic transducer in an alternating pattern. In particular embodiments, the processor may be configured to alternatingly transmit electric signals to the ultrasonic for between 5 to 50 frequency cycles, and then receive electric signals from the ultrasonic transducer for between 1 to 10 frequency cycles. In specific embodiments, the processor may be configured to transmit electric signals to a piezoelectric crystal of an ultrasonic transducer and receive electric signals from the piezoelectric crystal of the ultrasonic transducer.

The term "coupled" is defined as connected, although not necessarily directly, and not necessarily mechanically. Two items are "coupleable" if they can be coupled to each other, and, when coupled, may still be characterized as "coupleable." Unless the context explicitly requires otherwise, items that are coupleable are also decoupleable, and vice-versa. One non-limiting way in which a first structure is coupleable to a second structure is for the first structure to be configured to be coupled (or configured to be coupleable) to the second structure.

The terms "a" and "an" are defined as one or more unless this disclosure explicitly requires otherwise.

The term "substantially" and its variations (e.g., "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, a system that comprises an ultrasonic transducer has one sample reservoir unit, but may have more than one ultrasonic transducer.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
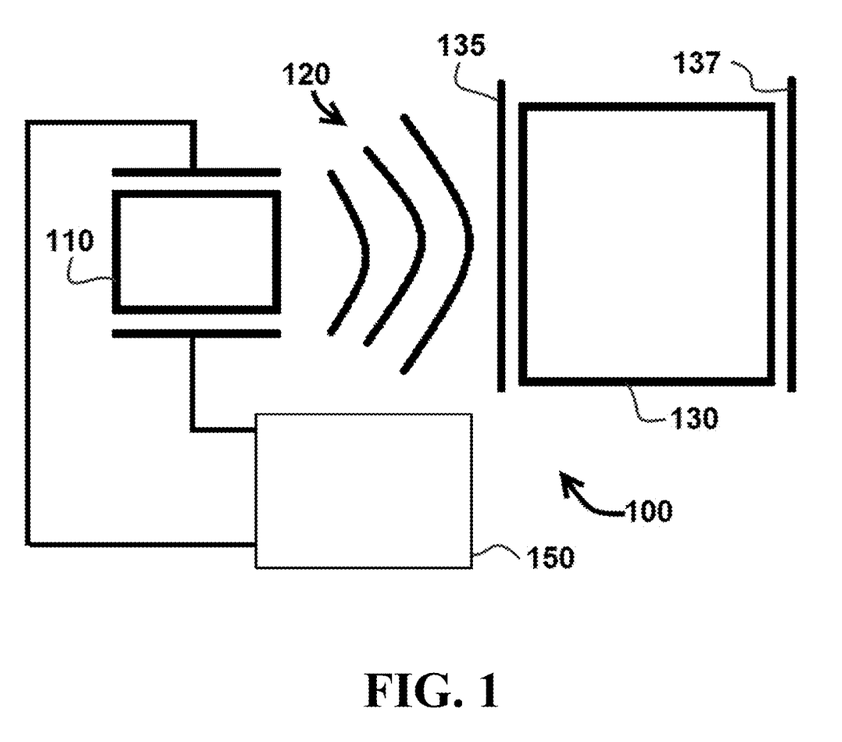
FIG. 1 is a schematic of an exemplary embodiment comprising an ultrasonic transducer operating in a first mode.
Figure 2:
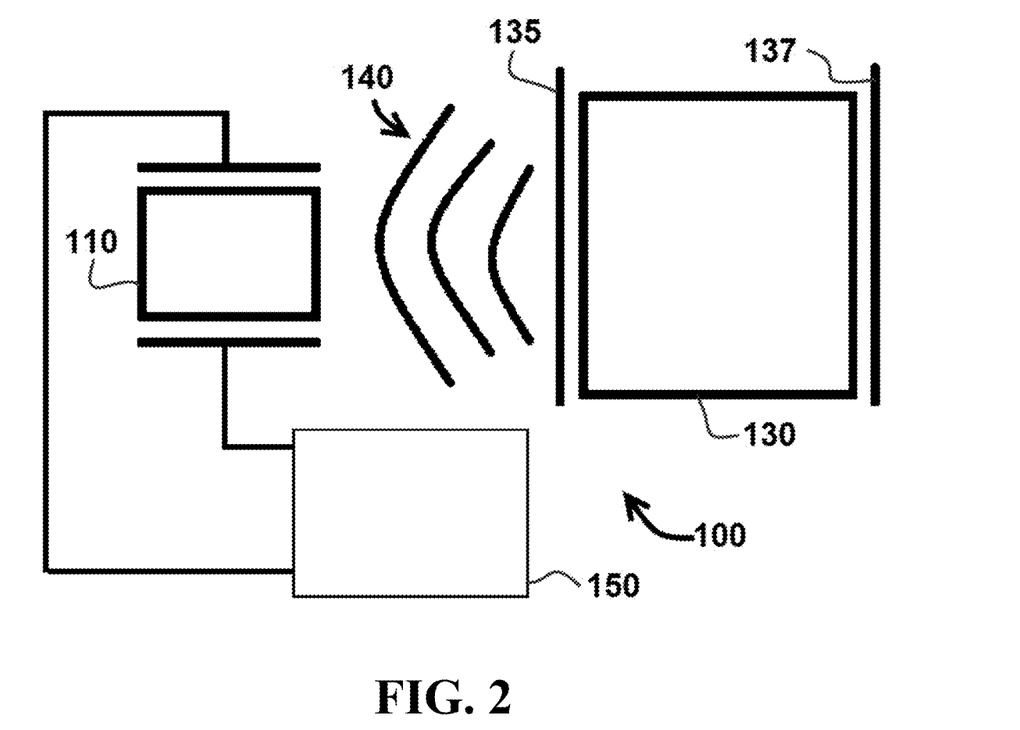
FIG. 2 is a schematic of the embodiment of FIG. 1 operating in a second mode.

Referring now to FIGS. 1 and 2, a cell lysis system 100 comprises an ultrasonic transducer 110 configured to transmit acoustic energy 120 to a chamber 130 and to receive reflected acoustic energy 140 from chamber 130. In certain embodiments, system 100 may comprise a coupling interface 135 configured to transmit acoustic energy 140 from ultrasonic transducer 110 into chamber 130. In particular embodiments, coupling interface 135 may comprise a spring coupling ultrasonic transducer 110 and chamber 130, while in other embodiments, coupling interface 135 may comprise a direct coupling between ultrasonic transducer 110 and chamber 130. In exemplary embodiments, the coupling method for applying an ultrasonic transducer to a sample chamber could be spring based or directly coupled to the cartridge.

In addition, system 100 may comprise a reflecting surface 137 configured to reflect acoustic energy 140 from chamber 130 to ultrasonic transducer 110. In some embodiments, reflecting surface 137 may have an acoustic impedance that is five, ten, twenty, or fifty percent different than the acoustic impedance of chamber 130 (e.g., in particular the wall of chamber 130 that is opposite of ultrasonic transducer 110). Such a configuration can increase the amount of acoustic energy 140 reflected back toward ultrasonic transducer 110.

Figure 3:
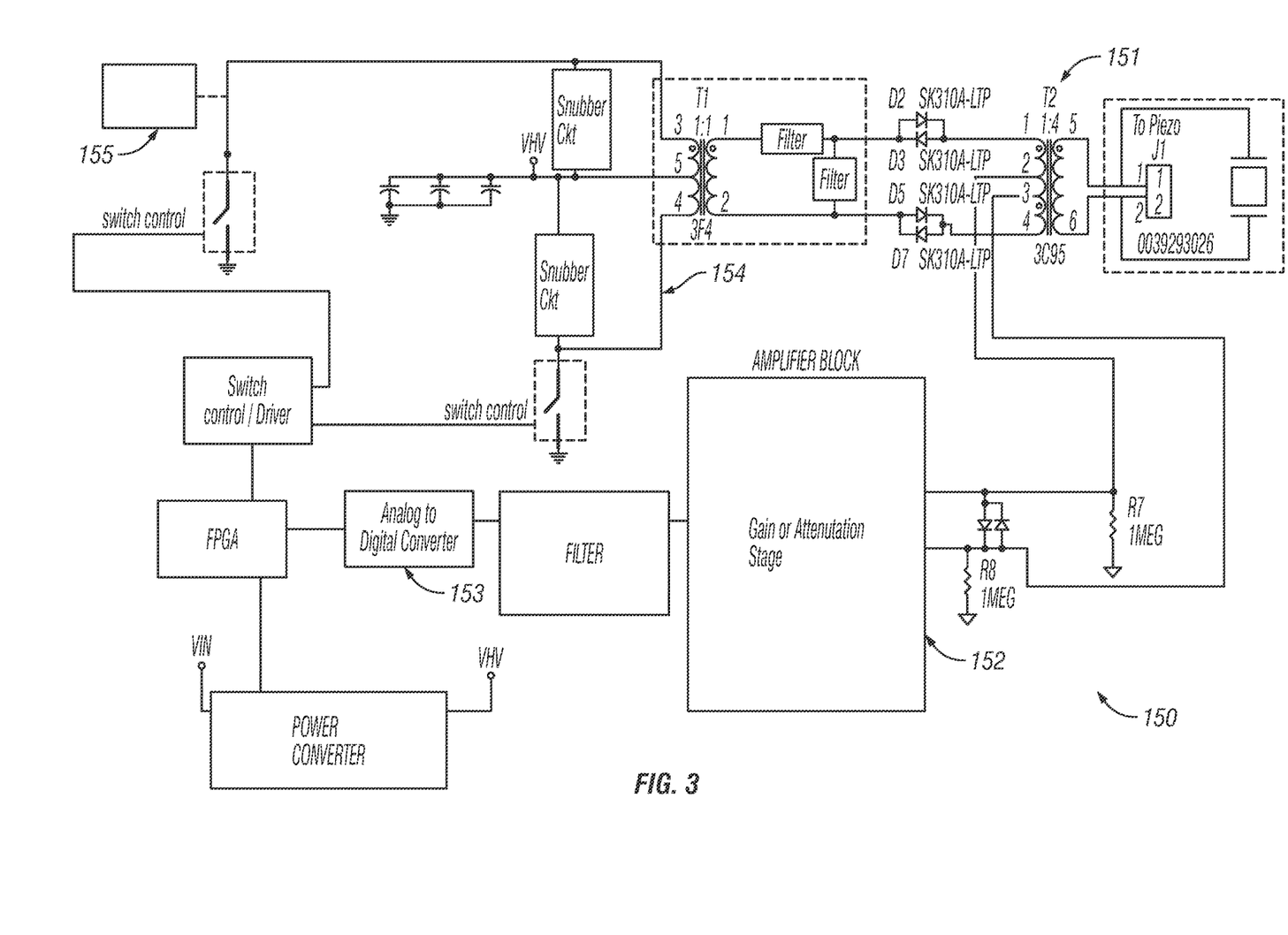
FIG. 3 is a schematic of an electronic circuit configured for use with the embodiment of FIG. 1.

In the embodiment shown, transducer 110 is coupled to an electronic control circuit 150 configured to control the transmitting and receiving functions of ultrasonic transducer 110. In a specific embodiment, electronic control circuit 150 may be configured as shown in FIG. 3, described in further detail below. It is understood that the configuration shown in FIG. 3 is merely one example of a component configuration, and that other embodiments may have different components, or a different arrangement of the illustrated components in an electronic control circuit.

During operation of cell lysis system 100, ultrasonic transducer 110 can be operated to transmit acoustic energy 120 at a series of transmission frequencies into chamber 130 as shown in FIG. 1. In addition, as shown in FIG. 2, ultrasonic transducer 110 can be operated to receive and measure reflected acoustic energy 140 from chamber 130 at multiple transmission frequencies (e.g., transducer can transmit acoustic energy 120 at several different transmission frequencies and receive and measure reflected acoustic energy 140 corresponding to each of the different transmission frequencies). In certain embodiments, ultrasonic transducer 110 may be configured to transmit and receive acoustic energy via a piezoelectric crystal.

In particular embodiments, acoustic energy 120 can be transmitted in a series of transmission frequencies spanning a range of 10 kHz-100 kHz. In specific embodiments, acoustic energy 120 can be transmitted in a series of transmission frequencies spanning a range of 30 kHz-60 kHz. Electronic control circuit 150 can be configured to provide a series of transmission frequencies in finite frequency stepped responses and/or a frequency-modulated (FM) sweep. The frequency of the electrical signal applied to ultrasonic transducer 110 can produce an acoustic signal of an equivalent frequency. As explained in further detail below, this adjustable range can allow a user to sweep values until a maximum peak value for energy dissipation is determined.

System 100 can be operated to determine an optimized transmit frequency, e.g. a transmit frequency for acoustic energy 120 that produces a minimized value of reflected acoustic energy 140 from chamber 130. The optimized transmit frequency that produces the minimized value of reflected acoustic energy 120 will also provide a maximized level of acoustic energy transmitted into chamber 130. Accordingly, the optimized transmit frequency can also provide efficient lysis of cells contained within chamber 130.

In certain embodiments, system 100 can be operated so that ultrasonic transducer 100 transmits acoustic energy 120 at transmit frequency corresponding to a particular ratio [i.e., a reflection coefficient $(R) = (I_{reflected})/(I_{transmitted})$] of the intensity of reflected acoustic energy 140 ($I_{reflected}$) to the intensity of transmitted acoustic energy 120 ($I_{transmitted}$). In particular embodiments, ultrasonic transducer 100 can be operated at a transmit frequency corresponding to a maximum reflection coefficient (R), while in other embodiments, ultrasonic transducer 100 can be operated a transmit frequency corresponding to a minimum reflection coefficient (R).

In particular embodiments system 100 can be operated so that ultrasonic transducer 100 transmits acoustic energy 120 at particular transmit frequency or reflection coefficient (R) corresponding to a specific cell or virus type contained within chamber 130. For example, ultrasonic transducer 100 can be operated to transmit acoustic energy 120 into chamber 130 containing a specified cell and/or virus at a predetermined frequency corresponding to a predetermined reflection coefficient ($R_{predetermined}$) for the specified cell type. The predetermined frequency for a particular cell and/or virus can be selected, for example, to provide optimum lysing times. Some embodiments may comprise storing an identifier of the known cell type, the transmit frequency, and the minimum or maximum determined value of R in a relational database.

In specific embodiments, ultrasonic transducer 110 can be operated intermittently to receive reflected acoustic energy 140 from chamber 130 to determine a calculated reflection coefficient ($R_{calculated}$). Ultrasonic transducer 110 can be continued to operate at the predetermined frequency if the calculated reflection coefficient ($R_{calculated}$) is within a predefined range of the predetermined reflection coefficient ($R_{predetermined}$). If the calculated reflection coefficient ($R_{calculated}$) is outside the predefined range of the predetermined reflection coefficient ($R_{predetermined}$), the transmit frequency of ultrasonic transducer 110 can be adjusted until the calculated reflection coefficient ($R_{calculated}$) is within the predefined range of the predetermined reflection coefficient ($R_{predetermined}$). Operation of ultrasonic transducer 110 can be terminated after a predetermined period of time, or a period of time sufficient to lyse the specified cell and/or virus located in chamber 130.

In exemplary embodiments, electronic control circuit 150 is configured to switch quickly between receive and transmit modes to accurately measure reflected acoustic energy 140.

The embodiment of electronic control circuit 150 provided in FIG. 3 is one configuration that provides for such capabilities. In exemplary embodiments, transducer 110 will not transmit acoustic energy 120 while receiving reflected acoustic energy 140 due to saturation that can occur on the receiver components in electronic control circuit 150. Therefore, system 100 and electronic control circuit 150 can be configured to interleave the transmit and receive measurements to obtain the response.

In the embodiment shown, electronic control circuit 150 comprises a switch 151, an amplifier circuit 152, an analog-to-digital converter 153, a power amplifier circuit 154, and a processor 155. In particular embodiments, processor 155 can be programmed with instructions to control the power amplifier circuit, and may be configured as a microprocessor, microcontroller, field-programmable gate array, or digital signal processor.

In particular embodiments, switch 151 may be configured as a multi-wound transformer, a single-wound transformer, or a solid state switching device. In certain embodiments, power amplifier circuit 152 may comprise a field-effect transistor 156.

Figure 7:
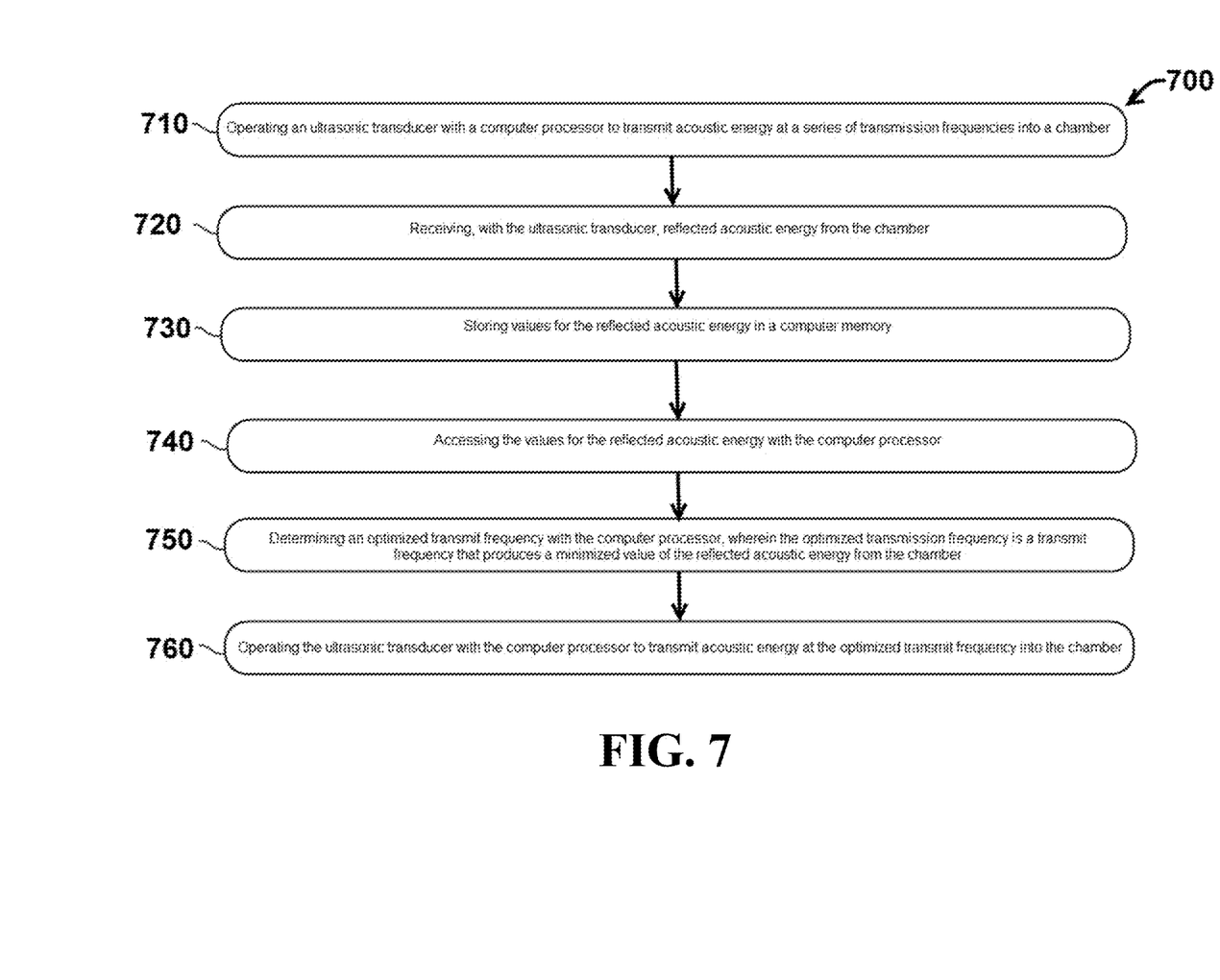
FIG. 7 is a schematic flowchart of steps in a method utilizing the embodiment of FIG. 1.

In particular embodiments, system 100 may be operated using a computer-implemented method (e.g. via processor 155). Referring now to FIG. 7, a flowchart of steps in one exemplary computer-implemented method 700 is provided. In this embodiment, method 700 comprises a step 710 of operating an ultrasonic transducer with a computer processor to transmit acoustic energy at a series of transmission frequencies into a chamber. Method 700 further requires step 720 of receiving, with the ultrasonic transducer, reflected acoustic energy from the chamber. Method 700 can also comprise step 730 of storing values for the reflected acoustic energy in a computer memory and step 740 of accessing the values for the reflected acoustic energy with the computer processor. Method 700 may also comprise step 750 of determining an optimized transmit frequency with the computer processor, where the optimized transmission frequency is a transmit frequency that produces a minimized value of the reflected acoustic energy from the chamber. In addition, method 700 may comprise step 760 of operating the ultrasonic transducer with the computer processor to transmit acoustic energy at the optimized transmit frequency into the chamber.

Figure 4:
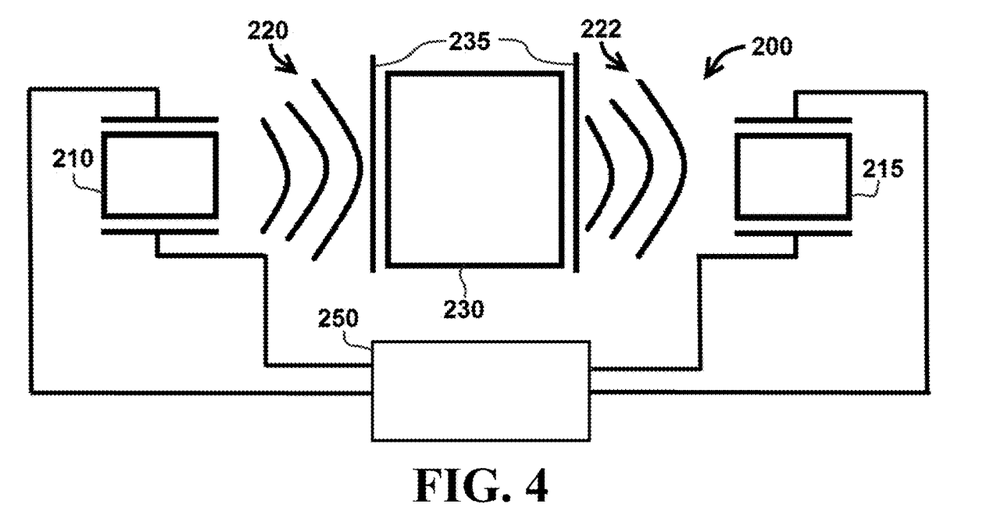
FIG. 4 is a schematic of an exemplary embodiment comprising two ultrasonic transducers operating in a first mode.
Figure 5:
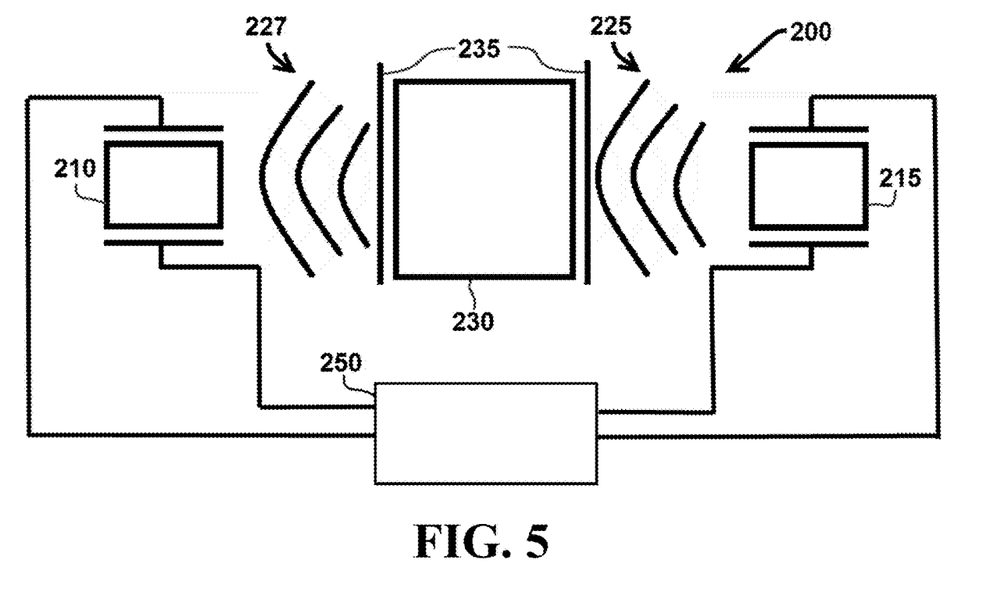
FIG. 5 is a schematic of the embodiment of FIG. 4 operating in a second mode.
Figure 6:
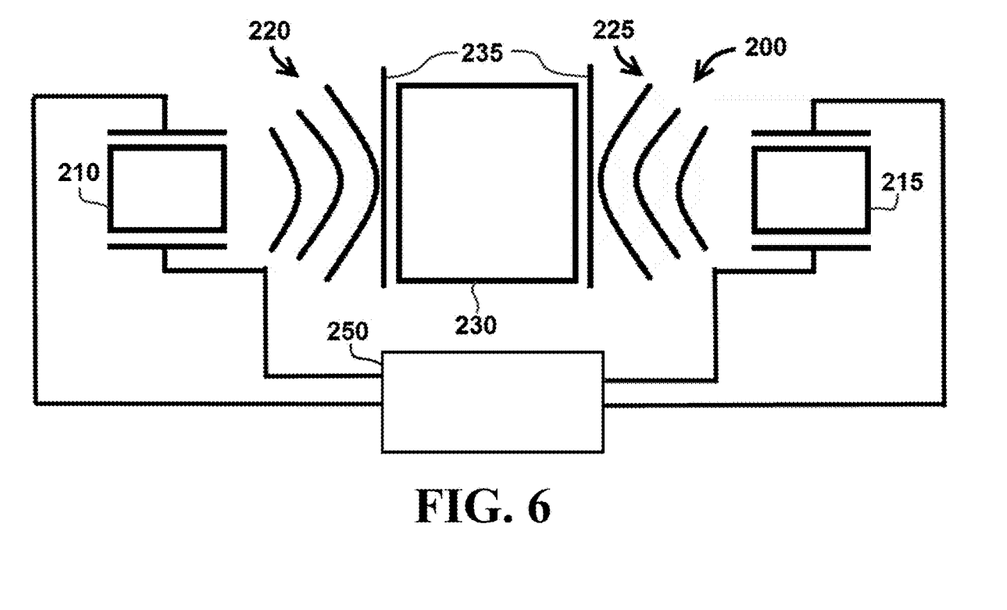
FIG. 6 is a schematic of the embodiment of FIG. 4 operating in a third mode.

Referring now to FIGS. 4-6, a cell lysis system 200 operates in a manner similar to the previously described system 100, but includes a first ultrasonic transducer 210 and a second ultrasonic transducer 215. Cell lysis system 200 does not utilize a single ultrasonic transducer to transmit and receive acoustic energy. Instead, as shown in FIG. 4, cell lysis system 200 utilizes first ultrasonic transducer 210 to transmit acoustic energy 220 into sample chamber 230 and second ultrasonic transducer 215 to receive acoustic energy 222 (e.g., the portion of acoustic energy 220 that is transmitted through sample chamber 230 and received by ultrasonic transducer 215). First and second ultrasonic transducers 210 and 215 can be coupled to an electronic control circuit 250 configured to control the transmitting and receiving functions of the ultrasonic transducers.

As shown in FIG. 5, cell lysis system 200 can also be operated such that second ultrasonic transducer 215 transmits acoustic energy 225 into sample chamber 230 and first ultrasonic transducer 210 receives acoustic energy 227 (e.g., the portion of acoustic energy 225 that is transmitted through sample chamber 230 and received by ultrasonic transducer 210). In particular embodiments, system 200 may comprise one or more coupling interfaces 235 configured to transmit acoustic energy 220 and 225 from ultrasonic transducers 210 and 215 into chamber 230.

Cell lysis system 200 can be operated so that first and second ultrasonic transducers 210 and 215 transmit acoustic energy 220 and 225, respectively, at a series of frequencies. An optimized transmit frequency for first ultrasonic transducer 210 can be determined by finding the transmit frequency that results in a minimum value of acoustic energy 222 received by second ultrasonic transducer 215. Similarly, an optimized transmit frequency for second ultrasonic transducer 215 can be determined by finding the transmit frequency that results in a minimum value of acoustic energy 227 received by first ultrasonic transducer 210. The optimized transmit frequency for each of the first and second ultrasonic transducers 210 and 215 corresponds to a maximum value of acoustic energy applied to contents within chamber 230.

Referring now to FIG. 6, cell lysis system 200 can be operated so that first and second ultrasonic transducers 210 and 215 each transmit acoustic energy 220 and 225, respectively, at optimized transmit frequencies. In certain embodiments, the optimized transmit frequencies for acoustic energy 220 and 225 can be simultaneously transmitted by first and second ultrasonic transducers 210 and 215, respectively. In particular embodiments, the optimized transmit frequencies for acoustic energy 220 and 225 can be transmitted by first and second ultrasonic transducers 210 and 215, respectively, in an alternating pattern.

In particular embodiments, first and second ultrasonic transducers 210 and 220 can be operated to transmit the first and second optimized transmit frequencies into sample chamber 230 for a predetermined amount of time. In certain embodiments, the predetermined period of time may be between 5 seconds and 5 minutes, or between 10 seconds and 2 minutes.

Figure 8:
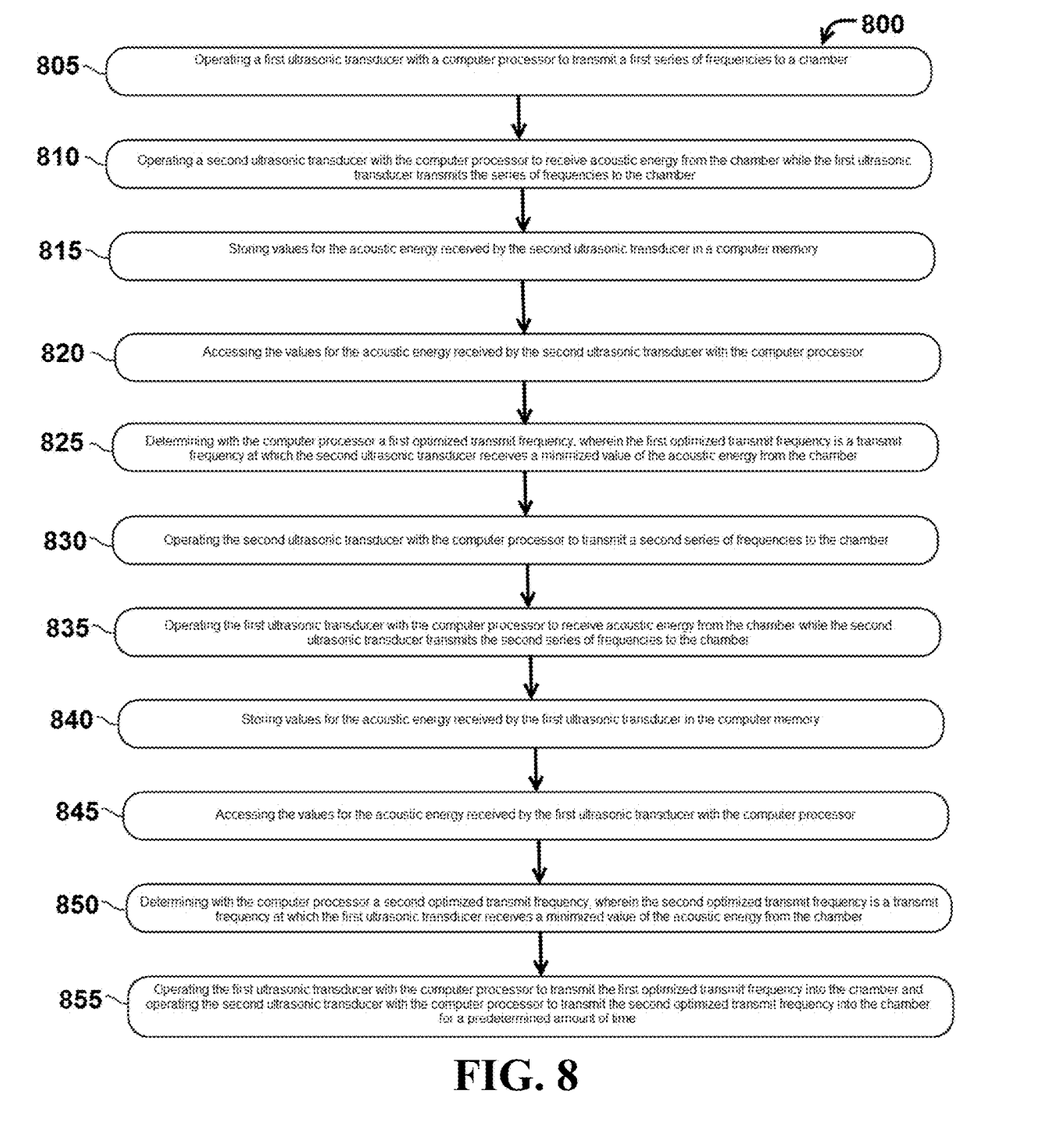
FIG. 8 is a schematic flowchart of steps in a method utilizing the embodiment of FIG. 4.

In particular embodiments, system 200 may be operated using a computer-implemented method. Referring now to FIG. 8, a flowchart of steps in one exemplary computer-implemented method 800 is provided. In this embodiment, method 800 comprises a step 805 of operating a first ultrasonic transducer with a computer processor to transmit a first series of frequencies to a chamber. Method 800 may also comprise step 810 of operating a second ultrasonic transducer with the computer processor to receive acoustic energy from the chamber while the first ultrasonic transducer transmits the series of frequencies to the chamber. In this embodiment, method 800 may comprise step 815 of storing values for the acoustic energy received by the second ultrasonic transducer in a computer memory and step 820 of accessing the values for the acoustic energy received by the second ultrasonic transducer with the computer processor. Method 800 may also comprise step 825 of determining with the computer processor a first optimized transmit frequency, wherein the first optimized transmit frequency is a transmit frequency at which the second ultrasonic transducer receives a minimized value of the acoustic energy from the chamber. Method 800 may also comprise step 830 of operating the second ultrasonic transducer with the computer processor to transmit a second series of frequencies to the chamber. Method 800 may further comprise step 835 of operating the first ultrasonic transducer with the computer processor to receive acoustic energy from the chamber while the second ultrasonic transducer transmits the second series of frequencies to the chamber. Method 800 may further comprise step 840 of storing values for the acoustic energy received by the first ultrasonic transducer in the computer memory and step 845 of accessing the values for the acoustic energy received by the first ultrasonic transducer with the computer processor. In certain embodiments, method 800 may also comprise step 850 of determining with the computer processor a second optimized transmit frequency, wherein the second optimized transmit frequency is a transmit frequency at which the first ultrasonic transducer receives a minimized value of the acoustic energy from the chamber. In addition, method 800 may comprise step 855 of operating the first ultrasonic transducer with the computer processor to transmit the first optimized transmit frequency into the chamber and operating the second ultrasonic transducer with the computer processor to transmit the second optimized transmit frequency into the chamber for a predetermined amount of time.

It should be understood that the present devices and methods are not intended to be limited to the particular forms disclosed. Rather, they are to cover all modifications, equivalents, and alternatives falling within the scope of the claims. For example, in certain embodiments more than two ultrasonic transducers may be utilized. In addition, other embodiments may use a control circuit that comprises different components from those disclosed herein.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references are incorporated herein by reference:
U.S. Pat. No. 6,819,027
U.S. Pat. No. 7,687,039
U.S. Pat. No. 8,115,366

I claim:

1. A method comprising:
    (a) operating an ultrasonic transducer to transmit, into a chamber containing a specified cell and/or virus, acoustic energy at a predetermined frequency corresponding to a predetermined reflection coefficient ($R_{predetermined}$) for the specified cell and/or virus type, wherein the reflection coefficient is a ratio of reflected acoustic energy intensity ($I_{reflected}$) and transmitted acoustic energy intensity ($I_{transmitted}$) and wherein a wall of the chamber opposite the ultrasonic transducer is adjacent to a reflecting surface that comprises a material that reflects ultrasonic energy and wherein the reflecting surface has an acoustic impedance that is at least five percent different than an acoustic impedance of the wall of the chamber opposite the ultrasonic transducer;
    (b) intermittently operating the ultrasonic transducer to receive reflected acoustic energy from the chamber, wherein the ultrasonic transducer alternatingly transmits the acoustic energy, then receives the reflected acoustic energy;
    (c) determining a calculated reflection coefficient ($R_{calculated}$) as the ratio of the reflected acoustic energy intensity in step (b) and the transmitted acoustic energy intensity in step (a);
    (d) continuing to operate the ultrasonic transducer at the predetermined frequency if the calculated reflection coefficient ($R_{calculated}$) is within a predefined range of the predetermined reflection coefficient ($R_{predetermined}$) or, if the calculated reflection coefficient ($R_{calculated}$) is outside the predefined range of the predetermined reflection coefficient ($R_{predetermined}$), adjusting the transmit frequency of the ultrasonic transducer until the calculated reflection coefficient ($R_{calculated}$) is within the predefined range of the predetermined reflection coefficient ($R_{predetermined}$); and
    (e) terminating operation of the ultrasonic transducer after a period of time sufficient to lyse the specified cell and/or virus.

2. The method of claim 1, wherein adjusting the transmit frequency of the ultrasonic transducer comprises:
    (a) operating the ultrasonic transducer to transmit acoustic energy at a series of transmission frequencies into the chamber; and
    (b) receiving, with the ultrasonic transducer, reflected acoustic energy from the chamber.

3. The method of claim 2, wherein the ultrasonic transducer alternatingly transmits acoustic energy for between 5 to 50 frequency cycles, then receives reflected acoustic energy for between 1 to 10 frequency cycles.

4. The method of claim 2, wherein the series of transmission frequencies spans a range of 10 kHz 100 kHz.

5. The method of claim 2, wherein acoustic energy is transmitted at a series of transmission frequencies with finite frequency steps.

6. The method of claim 2, wherein acoustic energy is initially transmitted at the series of transmission frequencies at 5 kHz increments.

7. The method of claim 6, wherein acoustic energy is subsequently transmitted at 1 kHz increments between two transmission frequencies of the series of transmission frequencies that produced the lowest two values of reflected energy from the chamber.

8. The method of claim 2, wherein the series of transmission frequencies is transmitted as a frequency-modulated (FM) sweep.

9. The method of claim 2, wherein the operating the ultrasonic transducer to transmit acoustic energy at the series of transmission frequencies into the chamber and the receiving acoustic energy with the ultrasonic transducer from the chamber is completed in less than 10 seconds.

10. The method of claim 1 wherein the predetermined frequency is selected to provide optimum lysing times.

11. The method of claim 1 further comprising:
    (f) storing an identifier of the specified cell and/or virus type, the predetermined frequency, and a minimum or maximum determined value of the predefined range of the predetermined reflection coefficient ($R_{predetermined}$) in a relational database.

12. The method of claim 1, wherein a wall of the chamber opposite the ultrasonic transducer comprises a material that reflects ultrasonic energy.

13. The method of claim 1 wherein the reflecting surface has an acoustic impedance that is at least ten percent different than an acoustic impedance of the wall of the chamber opposite the ultrasonic transducer.

14. The method of claim 1 wherein the reflecting surface has an acoustic impedance that is at least twenty percent different than an acoustic impedance of the wall of the chamber opposite the ultrasonic transducer.

15. The method of claim 1 wherein the reflecting surface has an acoustic impedance that is at least fifty percent different than an acoustic impedance of the wall of the chamber opposite the ultrasonic transducer.

16. The method of claim 1 wherein the ultrasonic transducer does not transmit acoustic energy while the ultrasonic transducer receives reflected acoustic energy.

17. The method of claim 1 wherein the ultrasonic transducer interleaves transmitting and receiving acoustic energy.

* * * * *

UNITED STATES PATENT AND TRADEMARK OFFICE
CERTIFICATE OF CORRECTION

PATENT NO. : 10,799,914 B2
APPLICATION NO. : 14/293024
DATED : October 13, 2020
INVENTOR(S) : Frederick Savage Page 1 of 1

It is certified that error appears in the above-identified patent and that said Letters Patent is hereby corrected as shown below:

In the Claims

In Claim 4, Column 14, Line 40, Please delete "10 kHz 100 kHz" and replace with --10 kHz - 100 kHz-- therefor.

Signed and Sealed this
First Day of December, 2020

Andrei Iancu
*Director of the United States Patent and Trademark Office*